United States Patent [19]

Silvestrini et al.

[11] Patent Number: 5,653,752
[45] Date of Patent: Aug. 5, 1997

[54] ADJUSTABLE DEVICES FOR CORNEAL CURVATURE ADJUSTMENT

[75] Inventors: Thomas Silvestrini, Alamo; Mark Mathis, Fremont; Bryan Loomas, Santa Clara, all of Calif.

[73] Assignee: KeraVision, Inc., Fremont, Calif.

[21] Appl. No.: 392,910

[22] Filed: Feb. 28, 1995

[51] Int. Cl.$^6$ ................................................. A61M 31/00
[52] U.S. Cl. ................................................. 623/5; 606/166
[58] Field of Search ..................... 623/4–5; 606/166, 606/167

[56] References Cited

U.S. PATENT DOCUMENTS

| | | |
|---|---|---|
| 4,298,004 | 11/1981 | Schachar et al. |
| 4,452,235 | 6/1984 | Reynolds . |
| 4,549,529 | 10/1985 | White . |
| 4,565,198 | 1/1986 | Koeniger . |
| 4,607,617 | 8/1986 | Choyce . |
| 4,646,720 | 3/1987 | Peyman et al. |
| 4,671,276 | 6/1987 | Reynolds . |
| 4,688,570 | 8/1987 | Kramer et al. |
| 4,766,895 | 8/1988 | Reynolds . |
| 4,782,820 | 11/1988 | Woods . |
| 4,815,463 | 3/1989 | Hanna . |
| 4,907,587 | 3/1990 | Fedorov et al. |
| 4,941,093 | 7/1990 | Marshall et al. |
| 4,961,744 | 10/1990 | Kilmer et al. |
| 5,066,301 | 11/1991 | Wiley . |
| 5,090,955 | 2/1992 | Simon . |
| 5,188,125 | 2/1993 | Kilmer et al. |
| 5,300,118 | 4/1994 | Silvestrini et al. |
| 5,312,424 | 5/1994 | Kilmer et al. |
| 5,372,580 | 12/1994 | Simon et al. |
| 5,466,260 | 11/1995 | Silvestrini et al. |

FOREIGN PATENT DOCUMENTS

| | | |
|---|---|---|
| 1597188 | 7/1988 | U.S.S.R. . |
| 2095119 | 9/1982 | United Kingdom . |

OTHER PUBLICATIONS

Blavatskaia, D.E.D., "The use of intralamellar homoplasty in order to reduce refraction of the eye" *Überstzt. Aus. Oftalmol. Zh.* (1966) 7:530–537 which was apparently translated to *Arch. Soc. Ophthmol. Optom.* (1988) 6:31–325.

English translation of Brazilian Patent Application No. BR 8705060 (Mar. 21, 1989).

Hartmann Chr., et al., "Intrastromale Implantation Eines Justierbaren Kunstsoffringes Zur Hornhautrefraktionsänderung", *KongreB der Deutschen Gesellschaft für Intraokularlinsen Implantation*, delivered by H. Freyler et al., Springer–Verlag, Wien pp. 465–475. The corresponding English language translation of the article namely, Hartmann, Chr., et al., Intrastromal implantation of an adjustable plastic ring to alter the corneal refraction *Congress for German Society for Intraocular Lens Implantation*, delivered by H. Freyler et al., (7 pages total).

(List continued on next page.)

*Primary Examiner*—Mary Beth Jones
*Attorney, Agent, or Firm*—Morrison & Foerster

[57] ABSTRACT

The intrastromal corneal ring is adjustable in thickness and has an elongated, flexible, preferably transparent or translucent body which forms a circle. The intrastromal corneal ring is of a size such that it can be inserted into a human eye and is comprised of a material which is compatible with human ocular tissue. The thickness of the ring can be adjusted so that it is not necessary to stock a plurality of different rings of different sizes to be used in connection with a method of adjusting the shape of the cornea of the eye. A plurality of different embodiments of intrastromal corneal rings, including a spiral shaped intrastromal corneal ring, are disclosed each of which are adjustable in terms of their thickness. The thickness may be adjusted prior to the insertion of the intrastromal corneal ring into the cornea and may not be further adjustable after insertion. However, in accordance with preferred embodiments the intrastromal corneal ring is inserted at a thickness which is believed to be proper and may thereafter be further adjusted in order to precisely define the desired thickness and thereby more precisely adjust the shape of the cornea and focus the light entering the eye on the retina.

6 Claims, 7 Drawing Sheets

OTHER PUBLICATIONS

Simón, G., et al., "Long term in vivo topographic studies of gel injection adjustable keratoplasty (GIAK)" *Abstracts: The Association for Research in Vision and Ophthalmology*, Annual Meeting Abstract Issue, Sarasota, Florida, USA, May 2–May 7, 1993, p. 1248, (abstract 2679–52).

Simón, G., et al., "Refractive remodeling of the cornea by intrastromal rings" *Abstracts: Eighth International Congress of Eye Research*, Proceedings of the International Society for Eye Research, San Francisco, California, USA, Sep. 4–8, 1988, Vol. V, (abstract No. 47).

Simón, G., et al., "Refractive remodeling of the cornea by intrastromal rings" *The Association for Research in Vision and Ophthalmology*, Annual Spring Meeting, Sarasota, Florida, USA, Apr. 30–May 5, 1989, p. 187, (abstract 43).

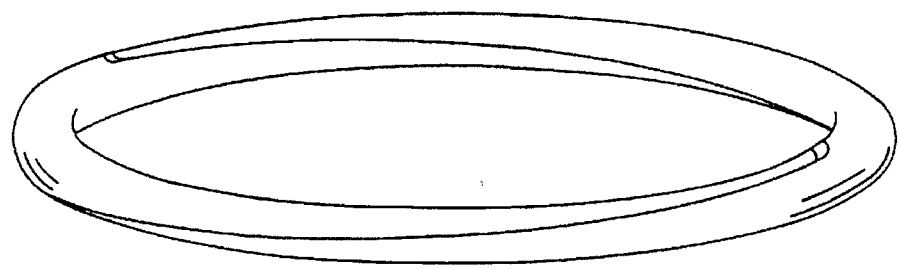
FIG.13
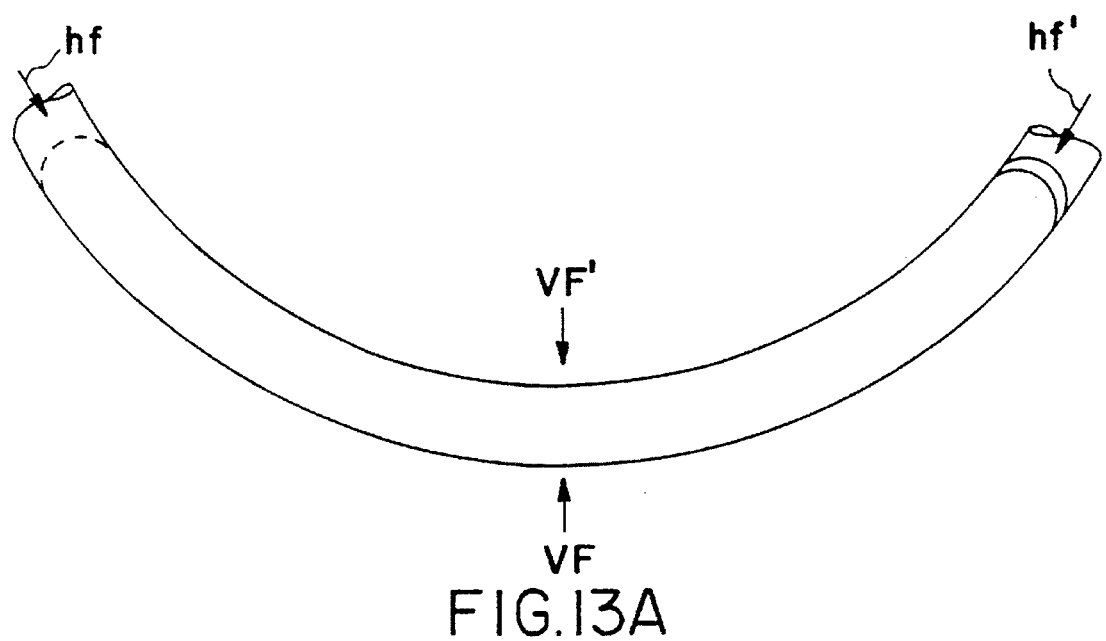
FIG.13A
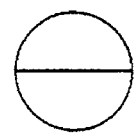 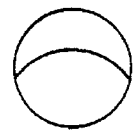 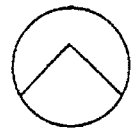
FIG.13B  FIG.13C  FIG.13D
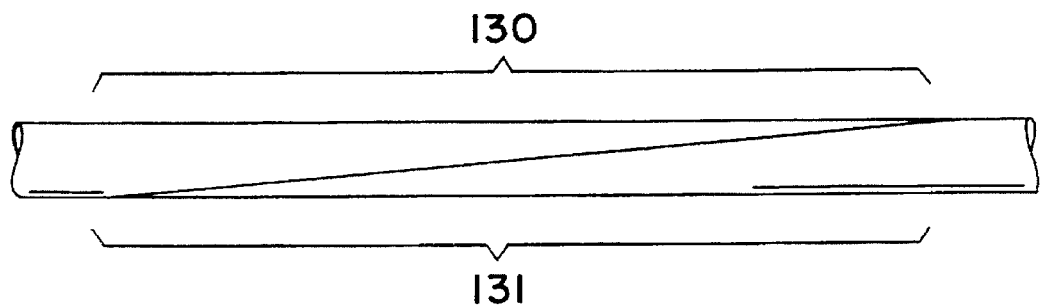
FIG.13E

ADJUSTABLE DEVICES FOR CORNEAL CURVATURE ADJUSTMENT

FIELD OF THE INVENTION

This invention is in the general field of medical technology and relates specifically to an intrastromal corneal ring designed such that its thickness can be varied in a manner so as to vary the corneal curvature to correct vision.

BACKGROUND OF THE INVENTION

Anomalies in the shape of the eye and specifically the shape as defined in part by the corneal can cause visual disorders. Hyperopia occurs when the eyeball is too short. In such a case, parallel rays from greater than 20 feet focus behind the retina. Myopia, on the other hand occurs when the eyeball is too long. The focus of parallel rays in this case is in front of the retina. Astigmatism is a condition in which the parallel rays of light do not come to a single point, but rather have a variable focus due to the fact that the cornea is aspherical and refracts light in a different meridian at different distances. Some degree of astigmatism is normal, but where it is too high, it must be corrected in order to provide acceptable vision.

Conditions such as hyperopia, myopia and astigmatism are usually corrected by glasses or contact lenses. Surgical methods for the correction of such disorders have been cited in the literature and include radial keratotomy (see e.g. U.S. Pat. Nos. 4,815,463 and 4,688,570) and laser corneal ablation (see e.g. U.S. Pat. No. 4,941,093). Further, the general method of implanting rings in the corneal stroma to change the curvature of the cornea is known. Previous work involving the implantation of polymethylmethacrylate (PMMA) rings, allograft corneal tissue and hydrogels is well documented. One of the ring devices involves a ring design that allows a split ring to be inserted into a channel. The channel is formed by dissecting the stromal layer of the cornea using a minimally invasive incision. Thereafter, the implant is inserted into the channel and the channel is sutured shut.

U.S. Pat. No. 4,452,235, which is herein incorporated by reference in its entirety, describes a method and apparatus for corneal curvature adjustment. The method involves inserting one end of a split end adjusting ring into the cornea of the eye and moving the ring in a circular path until its ends meet. The ends are thereafter adjusted relative to each other so that the ends can be connected. When so connected the shape of the eye will have assumed a desired curvature.

Various devices were required in order to facilitate the implantation of the rings of the type described in U.S. Pat. No. 4,452,235. Such a holder for inserting corneal curvature adjustable rings is described within U.S. Pat. No. 4,961,744 issued Oct. 9, 1990. Further, prior to inserting the ring it is necessary to cut an annular channel within the cornea and a device for cutting such a channel is disclosed within U.S. Pat. No. 4,766,895 issued Oct. 30, 1988.

Other devices for adjusting the corneal curvature have been disclosed such as the device shown within U.S. Pat. No. 4,671,276 issued Jun. 9, 1987. In addition, devices for affecting other parts of the eye such as an iris retaining device are disclosed within U.S. Pat. No. 4,782,820 issued Nov. 8, 1988 and a variable focus lens which is disclosed within U.S. Pat. No. 5,066,301 issued Nov. 19, 1991. More recently a method of changing cornea curvature by injecting a gel into the cornea was disclosed in U.S. Pat. No. 5,090,955 issued Feb. 25, 1992.

The present invention describes split ring devices which are inserted in the corneal stroma and have adjustable thicknesses which provide certain advantages and improvements as compared to earlier intrastromal corneal rings.

SUMMARY OF THE INVENTION

The present invention is an intrastromal corneal ring of adjustable thickness which has an elongated, flexible body which forms a circle. The intrastromal corneal ring is of a size such that it can be inserted into a human eye and specifically into the outer periphery of the cornea of a human eye. The intrastromal corneal ring is comprised of a material which is compatible with human ocular tissue and specifically compatible with corneal tissue. The means for adjusting the thickness of the ring may be formed in several different configurations or embodiments. Two open ended annular body members may be interconnected in such a manner that the distance between the body members can be adjusted to provide different thicknesses and thereby obtain different degrees of change in the shape of the eye effecting the focus of light on the retina.

The essence of the present invention lies in the ability of the ring to be adjusted in thickness so that it is not necessary to stock a plurality of different rings of different sizes to be used in connection with the method for adjusting the shape of the cornea of a, eye. Accordingly, the present invention provides a plurality of different embodiments of ICRs which are each adjustable in terms of their thickness. The thickness adjustment may occur prior to the insertion of the intrastromal corneal ring into the cornea and my not be further adjustable after insertion. However, in the preferred embodiments of the invention the intrastromal corneal ring is inserted at a thickness which is believed to be proper and may be adjusted thereafter in order to precisely define the desired thickness and thereby more precisely adjust the shape of the cornea and focus the light entering the eye on the retina.

A primary object of the invention is to provide an intrastromal corneal ring having an adjustable thickness.

An advantage of the invention is that a single ring of adjustable thickness can be used thereby eliminating the need for multiple rings of different thickness.

A feature of the invention is that the ring thickness can be adjusted while the ring is in place.

Another advantage of the ring is that it can be readjusted at later times in order to readjust the curvature of the eye as needed.

These and other objects, advantages and features of the present invention will become apparent to those persons skilled in the art upon reading the details of the structure and operation as more fully set forth below, reference being made to the accompanying drawings forming a part hereof wherein like symbols refer to like components throughout.

BRIEF DESCRIPTION OF THE DRAWINGS

FIGS. 13, 13A, 13B, 13C, 13D and 13E are different views showing how the ends of the annular body member might overlap.

DETAILED DESCRIPTION OF THE INVENTION

Before the adjustable intrastromal corneal ring and its various embodiments and configurations and methods of use are described, it is to be understood that this invention is not limited to the particular embodiments, configurations, materials and steps described as such my, of course, vary. It is also to be understood that the terminology used herein is for the purpose of describing particular embodiments only and is not intended to be limiting, since the scope of the present invention will be limited only by the appended claims.

The basic structure, function and operation of the adjustable intrastromal corneal rings of the invention is shown and discussed in connection with FIGS. 1–6. FIGS. 7–15 show eight different embodiments of the invention which show six basic configurations whereby the rings can vary in terms of their thickness and/or height. Further, the ring ends can be connected to each other without the use of additional components in a manner so as to provide a smooth and continuous interconnection between the ends so that the surface of the ring appears substantially smooth and continuous along its entire surface even at the interconnection of the ring ends.

The different embodiments shown in FIGS. 7–15 can each include a number of different subembodiments by varying features such as the material, the manner in which the ring ends are interconnected and the cross sectional surface parameters of the ring e.g. forming the ring from cross sections in the form of a circle, square, rectangle, triangle, oval, etc. Although a number of configurations are shown others are possible and are contemplated by this invention. Further, other possible means of adjusting the ring thickness are contemplated by this invention. It is preferable if the invention is constructed such that the ring size can be adjusted while the ring is in place in the eye.

Before discussing the specific embodiments of FIGS. 7–15 the general structure and method of use of adjustable intrastromal corneal rings will be described in connection with FIGS. 1–4 and thereafter generalized information relating to the rings of the present invention in connection with FIGS. 5 and 6.

Figure 1:
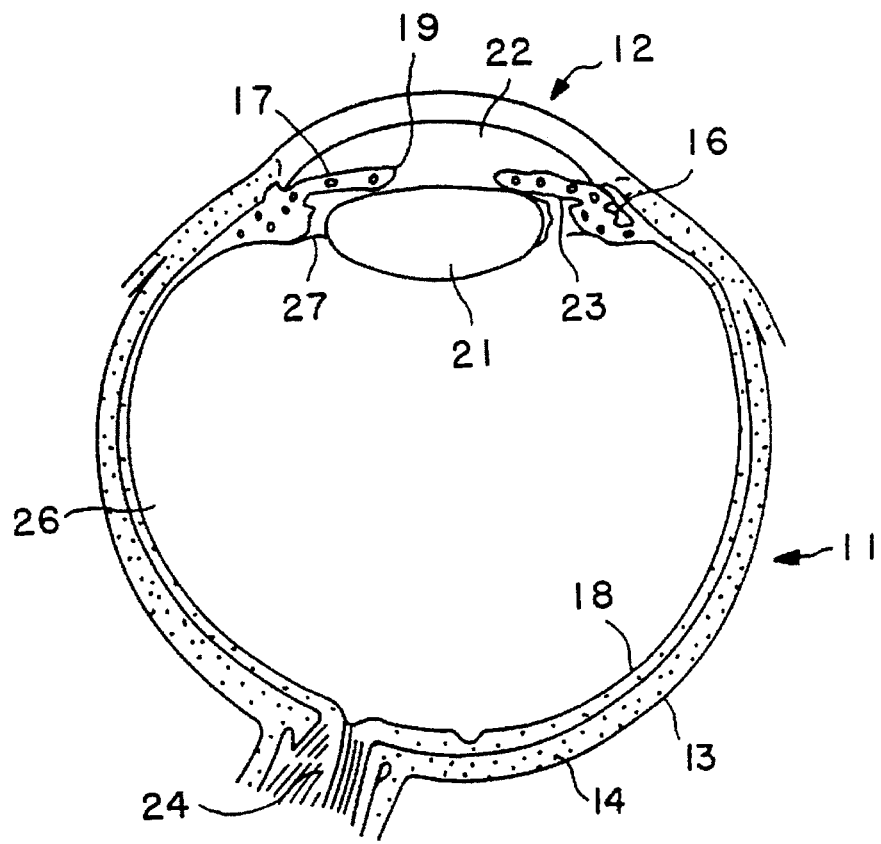
FIG. 1 is a schematic representation of a horizontal section of the eye.

FIG. 1 shows a horizontal section of the eye with the globe 11 of the eye resembling a sphere with an anterior bulged spherical portion representing the cornea 12.

The globe 11 of the eye consists of three concentric coverings enclosing the various transparent media through which the light must pass before reaching the sensitive retina 18. The outermost covering is a fibrous protective portion the posterior five-sixths of which is white and opaque and called the sclera 13, and sometimes referred to as the white of the eye where visible to the front. The anterior one-sixth of this outer layer is the transparent cornea 12.

A middle covering is mainly Vascular and nutritive in function and is comprised of the choroid 14, ciliary body 16 and iris 17. The choroid 14 generally functions to maintain the retina 18. The ciliary body 16 is involved in suspending the lens 21 and accommodation of the lens. The iris 17 is the most anterior portion of the middle covering of the eye and is arranged in a frontal plane. It is a thin circular disc corresponding to the diaphragm of a camera, and is perforated near its center by a circular aperture called the pupil 19. The size of the pupil varies to regulate the amount of light which reaches the retina 18. It contracts also to accommodation, which serves to sharpen the focus by diminishing spherical aberration. The iris 17 divides the space between the cornea 12 and the lens 21 into an anterior chamber 22 and posterior chamber 23. The innermost portion of covering is the retina 18, consisting of nerve elements which form the true receptive portion for visual impressions.

The retina 18 is a part of the brain arising as an outgrowth from the fore-brain, with the optic nerve 24 serving as a fiber tract connecting the retina part of the brain with the fore-brain. A layer of rods and cones, lying just beneath a pigmented epithelium on the anterior wall of the retina serve as visual cells or photoreceptor which transform physical energy (light) into nerve impulses.

The vitreous body 26 is a transparent gelatinous mass which fills the posterior four-fifths of the globe 11. At its sides it supports the ciliary body 16 and the retina 18. A frontal saucer-shaped depression houses the lens.

The lens 21 of the eye is a transparent biconvex body of crystalline appearance placed between the iris 17 and vitreous body 26. Its axial diameter varies markedly with accommodation. A ciliary zonule 27, consisting of transparent fibers passing between the ciliary body 16 and lens 21 serves to hold the lens 21 in position and enables the ciliary muscle to act on it.

Referring again to the cornea 12, this outermost fibrous transparent coating resembles a watch glass. Its curvature is somewhat greater than the rest of the globe and is ideally spherical in nature. However, often it is more curved in one meridian than another giving rise to astigmatism. A central third of the cornea is called the optical zone with a slight flattening taking place outwardly thereof as the cornea thickens towards its periphery. Most of the refraction of light striking the eye takes place as the light passes through the cornea.

Figure 2:
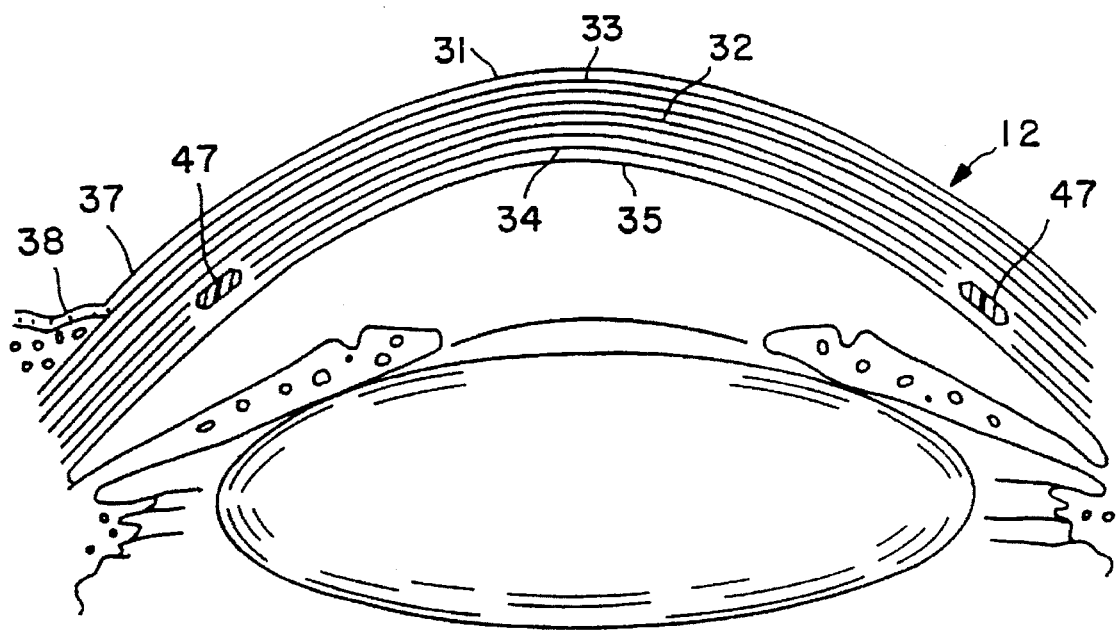
FIG. 2 is a schematic illustration of the anterior portion of the eye showing the various layers of the cornea with an intrastromal corneal ring inserted therein.

Referring to FIG. 2, a more detailed drawing of the anterior portion of the globe shows the various layers of the cornea 12 comprising an epithelium 31. Epithelial cells on the surface thereof function to act as the main protection layer of the cornea 12. These epithelial cells are rich in glycogen, enzymes and acetylcholine and their activity regulates the corneal corpuscles and controls the transport of water and electrolytes through the lamellae of the stroma 32 of the cornea 12.

An anterior limiting lamina 33, referred to as Bowman's membrane or layer, is positioned between the epithelium 31 and the stroma 32 of the cornea. The stroma 32 is comprised of lamella having bands of fibrils parallel to each other and crossing the whole of the cornea. While most of the fibrous bands are parallel to the surface, some are oblique, especially anteriorly. A posterior limiting lamina 34 is referred to as Descemet's membrane. It is a strong membrane sharply defined from the stroma 32 and resistant to pathological processes of the cornea.

The endothelium 36 is the most posterior layer of the cornea and consists of a single layer of cells which aid in maintaining the transparency of the cornea. The limbus 37 is the transition zone between the conjunctiva 38 and sclera 13 on the one hand and the cornea 12 on the other.

A cross sectional view of an intrastromal corneal ring 47 of the invention is shown within the stroma 32 of the cornea 12. The ring 47 is placed in the stroma 32 by making an initial incision into the cornea 12 and then continuing to separate the stroma of the cornea in a circular direction from the initial incision beneath the surface of the cornea so as to provide a complete annular channel within the cornea 12. The ring 47 is placed within the annular channel.

Figure 3:
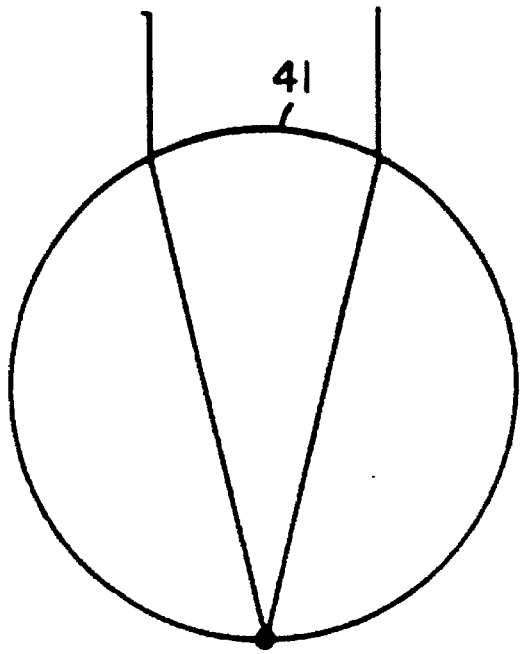
FIG. 3 is a schematic representation showing how light moves through a normal eye to focus on the retina.
Figure 4:
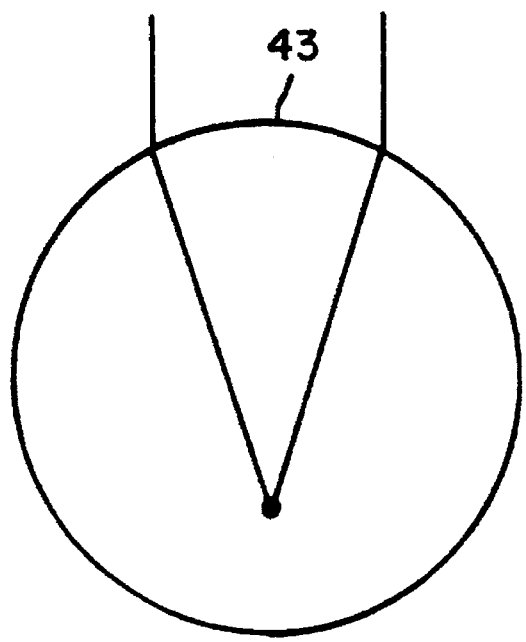
FIG. 4 is a schematic representation showing how light moves through a myopic eye and focuses in front of the retina.

FIG. 3 shows the globe of the eye having a cornea with a normal curvature 41. If parallel rays of light pass through the corneal surface 41 of FIG. 3, they are refracted by the corneal surfaces to converge eventually near the retina of the eye. The diagram of FIG. 3 discounts, for the purposes of this discussion, the refractive effect of the lens or other portions of the eye. The eye depicted in FIG. 4 is myopic. The corneal curvature 43 causes the light rays to refract into focus at a point in the vitreous body which is short of the retinal surface. If an intrastromal corneal ring is implanted into the chord of the cornea such that the radius of curvature of the cornea is uniformly increased, the central curvature of the cornea is flattened. Light rays refracted by the now flattened corneal surface will be refracted at a smaller angle and thus converge at a more distant point such as directly on the retina.

The intrastromal corneal rings of the present invention make it possible to adjust the radius of curvature of the cornea without adversely affecting its natural sphericity. Where there is serious astigmatism, the natural sphericity will not be altered such that the astigmatism will be significantly increased. However, where there is significant astigmatism that results in impaired vision, the intrastromal corneal ring of the invention may actually improve the sphericity to reduce such astigmatism and improve vision.

As is shown in FIGS. 3 and 4 by changing the curvature from a curvature 43 to a curvature 41 the focal point can be correctly positioned on the retina. A small degree of curvature change can affect the focal point of the light entering the eye. Accordingly, it is difficult to choose the correct thickness of an intrastromal corneal ring to be inserted in the stroma of the cornea so that it will correctly, affect the focal point of the light entering the eye. The difficulty with respect to choosing the correct thickness is the point where the advantages of the present invention become most apparent. When the present invention is used the intrastromal corneal ring is first adjusted to have a thickness which is believed to be the correct thickness. However, after inserting the ring into the stroma of the cornea the thickness of the ring can be further adjusted in order to precisely focus the light entering the eye on the retina.

Figure 6A:
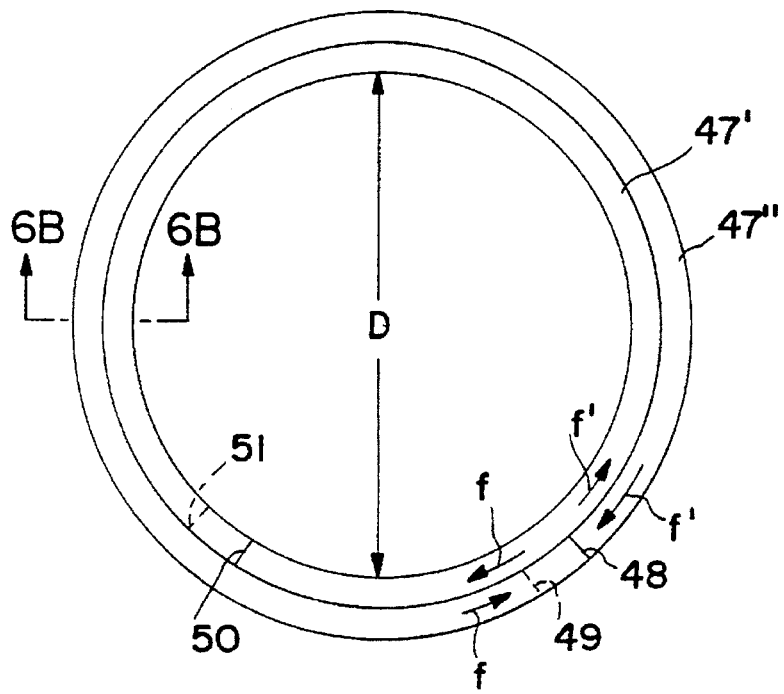
FIG. 6 includes a plane view (6A) and a perspective sectional view (6B) of an intrastromal corneal ring of the invention.
Figure 6B:
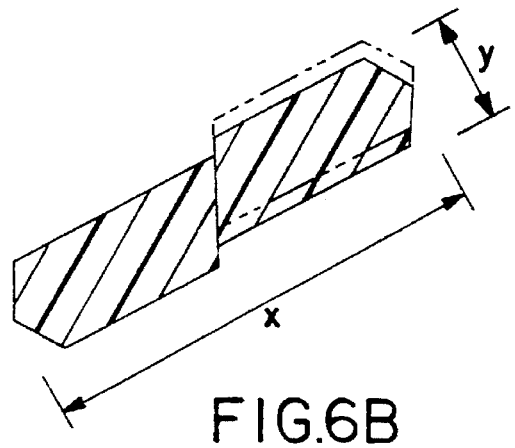

As shown in FIG. 2, an intrastromal corneal ring 47, having a cross sectional shape as shown in FIG. 6B is shown implanted in the stromal layer of the cornea. The thickness of the ring can be adjusted prior to placing the ring in the eye. Preferably the ring thickness can be further adjusted in situ to precisely adjust the amount of correction necessary. By such adjustments the rays refracted by the cornea and other eye components can be brought to focus directly on the retina (not shown in FIG. 2).

Figure 5:
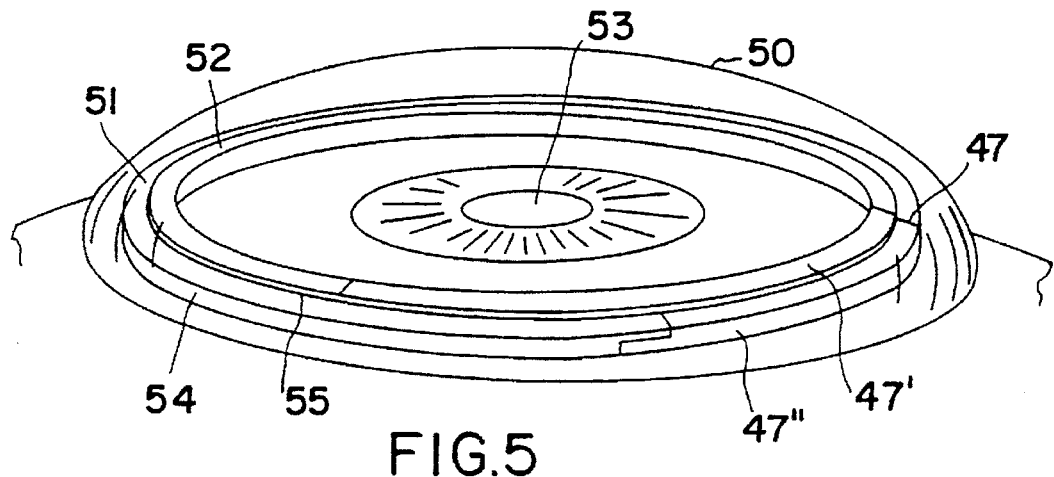
FIG. 5 is a perspective view of one embodiment of the intrastromal corneal ring of the invention inserted within a cornea of a human eye.

FIG. 5 shows a perspective view of the intrastromal corneal ring 47 with its threaded height adjustment means is inserted within a cornea 50 of a human eye. In the embodiment shown within FIG. 5, the intrastromal corneal ring is placed in a manner such that the widest faces 51 and 52 face outward along the line of sight 53 and away from the eye, whereas the narrower faces 54 and 55 face radially inward toward the center of the eye and the wide and narrow faces are perpendicular to each other. However, it should be noted that other configurations are possible. Height or thickness adjustment is carried out by screwing the threaded body members 47' and 47" so that they move away from or toward each other depending on whether an increase or decrease in thickness is required.

A plane view of the intrastromal corneal ring 47 of the invention is shown in FIG. 6A. As shown, the intrastromal corneal ring is circular in shape and is comprised of two elongated, flexible body members 47' and 47" each of which forms a circle. One possible cross sectional configuration is shown in FIG. 6B which configuration is basically rectangular with angled outer edges. Other cross sectional configurations are possible, such as square, circular, and variations therebetween. Because the body of the ring is circular, it has the same diameter D in all directions. However, it is possible to configure the body of the ring in other slightly noncircular configurations, e.g., ovals and elongated ovals. However, in these configurations the two rings are not interconnected by threading but by other adjustable means such as ratched slots. In its preferred circular configuration, the diameter conforms to the size of a human cornea which is approximately 1 cm in diameter. The ring is comprised of a biocompatible material such as a biocompatible polymer. Such biocompatible materials and polymers are particularly designed with eye tissue characteristics in mind. Accordingly, materials such as those used in making contact lenses can be used. It is pointed out that the ocular tissues is generally quite sensitive and my react upon the implantation of the ring. However, after a period of time, any inflammation and/or adverse reaction will be eliminated. In order to decrease the probability of adverse reactions, it is desirable to choose a biocompatible material which will not create an immune reaction, be nontoxic and biologically benign. Metals and metal alloys are generally undesirable as are other types of materials which react with the ocular tissue.

The rings 47' and 47" in FIG. 6A each show one end 48 and 50. Because FIG. 6A is a planar view, the ends 48 and 50 are each shown as a single line. The other ends 49 and 51 are each shown by a dotted line in that this end is visible only from the other side of the rings 47' and 47". The corresponding ends 48 and 49 and corresponding ends 50 and 51 may be structured in several different configurations, as discussed in connection with FIGS. 13 and 6A.

As shown in FIGS. 6A and 13, the corresponding ends 48 and 49 are overlapping each other as the ends 50 and 51. The rings can be screwed toward each other as shown by the arrows f or in the opposite direction as shown by the arrows f'.

The thickness of the ring my be between adjusted within a range of about 0.05 mm and 1.5 mm. Such a ring placed approximately at the 8 mm chord of the cornea provides a means for making such a corrective adjustment.

As indicated above FIGS. 5 and 6A show an intrastromal corneal ring of the invention which is comprised of a generally circular body member. The ring is comprised of a material which has sufficient stiffness to maintain its generally circular shape. The material should have properties that render it physiologically compatible with the tissue of the cornea. An illustrative material is a plastic type material sold under the trade name of PLEXIGLASS™, however many other biocompatible polymers are useful in the invention, including but not limited to polyolefins (e.g., polypropylene and polybutylene), polycarbonates, acrylic resins (e.g., acrylates and methacrylates, including polymethylmethacrylate (PMMA) and polyhydroxyethyl methacrylate (polyHEMA)), polyacetals, polyesters, polyamides (e.g., nylon), polyurethanes, epoxy resins, silicones or other natural or synthetic rubbers, copolymers that are composed of hard and soft segments (e.g., HYTREL, Dupont, Wilmington, Del.), polytetrafluoroethylene (PTFE), polyvinylpyrrolidone, polyethers/ether ketones, polysulfones, glass, and copolymers (discrete or block), blends and mixtures of the above. As discussed above, the means of adjusting ring thickness can vary. When a cross section of the ring is circular, it is generally dimensioned to be about 0.05 mm to 1.5 mm in thickness.

A particular cross sectional configuration is schematically shown in FIG. 6B. When this configuration is used, the dimension shown from point to point (dimension x) may be within the range of approximately 0.25 mm to 3.25 mm and the thickness (dimension y) generally can be adjusted in the range from about 0.05 mm to about 1.5 mm.

There are a number of factors which affect the degree of flattening of the cornea obtained depending upon the thickness of the ring being inserted. Accordingly, it is not always possible to deduce a direct relationship between the ring thickness and the degree of flattening and therefore the change in focal point. Variations are caused by factors such as the type of mammal in which the ring is being inserted and the size and shape of the eye. However, in certain experiments, it has been found that optical corrections can be carried out at the rate of 1 diopter of flattening for each 0.02 mm increase in intrastromal corneal ring thickness when the size of the ICR is in the range of about 0.26 mm to about 0.46 mm in thickness. Thus, it is advantageous to set the threading on the interconnected ring so that one 360°, 180°, or 90° turn of one ring relative to the other changes the thickness by 0.02 mm. Alternatively, in a ratched embodiment one increment change will change the thickness by 0.02 mm or some fraction or multiple thereof.

Even where the eye is not myopic, the intrastromal corneal rings of the present invention my be useful to alleviate excessive astigmatism.

A typical panel of intrastromal corneal rings will consist of 5 intrastromal corneal rings with the following thicknesses: 0.25 mm, 0.30 mm, 0.35 mm, 0.40 mm and 0.45 mm. The corrective refraction for those ICRs are as follows: between 0.5 and 3.0 diopters for the 0.25 mm intrastromal corneal rings, between 1.0 and 5.0 diopters for the 0.30 mm intrastromal corneal rings, between 2.0 and 8.0 diopters for the 0.35 mm intrastromal corneal ring, between 3.0 and 10.0 diopters for the 0.40 mm intrastromal corneal ring, and between 4.0 and 15.0 diopters for the 0.45 mm intrastromal corneal ring. It should be noted that these values are for conventional intrastromal corneal rings and that value of between 0.5 to 18.0 might be used. The amount of corrective refraction for the various thicknesses of intrastromal corneal rings of different cross sectional shaped rings may differ from those values.

The essence of the present invention lies in the ability of the ring to be adjusted in thickness so that it is not necessary to stock a plurality of different rings of different sizes to be used in connection with the method for adjusting the shape of the cornea of an eye. Accordingly, the present invention provides a plurality of different embodiments of intrastromal corneal rings which are each adjustable in terms of their thickness. The thickness adjustment my occur prior to the insertion of the intrastromal corneal ring into the cornea and my not be further adjustable after insertion. However, in the preferred embodiments of the invention the intrastromal corneal ring is inserted at a thickness which is believed to be proper and my be adjusted thereafter in order to precisely define the desired thickness and thereby more precisely adjust the shape of the cornea and focus the light entering the eye on the retina.

The intrastromal corneal ring is inserted into the corneal atroma of the eye through an oblique keratotomy incision placed peripherally into the corneal stroma. The size of the insertion will vary somewhat depending on factors such as the size of the ring or rings being inserted. In general, the size of the insertion is approximately 0.5 mm to 5.0 mm in length with an incision of approximately 2.5 mm being typical. Prior to ring insertion, a channeling blade is inserted at the depth of the incision and a circular channel is cut into the corneal stroma. Proper centering of the cut is accomplished by use of a centering device that aligns the channeling blade. The ring is then inserted and the ends are secured by fastening one end to the other.

SPECIFIC PREFERRED EMBODIMENTS

Eight different basic preferred embodiments are shown in FIGS. 7–15. In addition, many of the basic embodiments are further illustrated by means of subembodiments which include, for example, different configurations of the cross sectional parameter of the ring. It is emphasized that each of the embodiments and subembodiments my be interchanged and be comprised of different materials and provided in different sizes in accordance with the size limitations indicated above. Further, the disclosures of these different embodiments my demonstrate to others skilled in the art that other embodiments are possible which provide substantially the same results in terms of providing a ring structure which is adjustable in terms of its thickness.

Figure 7A:
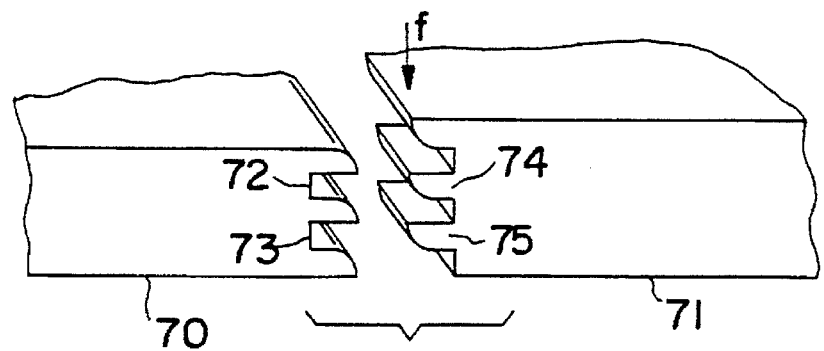
FIGS. 7A and 7B are perspective views showing a ratcheted height adjustment embodiment in two positions.
Figure 7B:
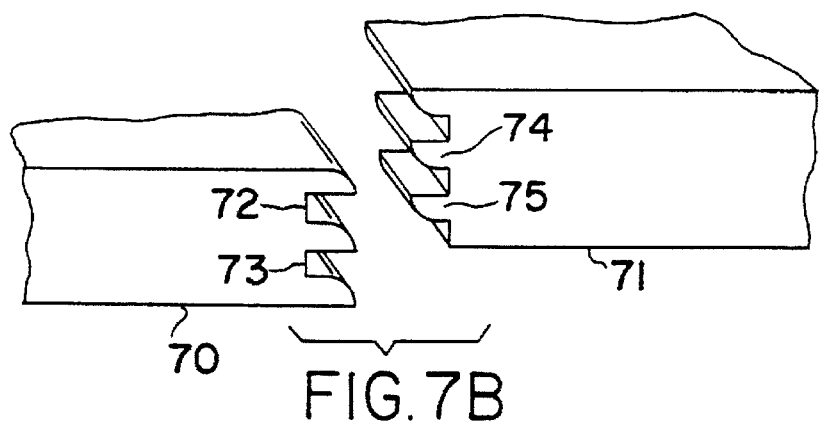

A ratched height adjustment embodiment is shown in FIGS. 7A and 7B. Cross sectional views of the embodiment in different relative positions to create thickness variations are shown in FIGS. 7A and 7B. The lower ring 70 is surrounded by the outer upper ring 71 and the two rings are interconnected by means of ratched slots 72 and 73 and protuberances 74 and 75. The protuberances 74 and 75 fit within the slots 72 and 73 respectively. The ring 71 can be pulled upward in the direction of the arrow f in order to reposition the protuberances 74 and 75 as shown within FIG. 7B. In the configuration shown within FIG. 7B the thickness of the dual ring structure is increased as compared with the thickness of the structure positioned as per FIG. 7A. This embodiment is simple to produce and provides desirable results as compared with the use of a multiplicity of different rings. However, the embodiment is not desirable in that it is somewhat difficult to adjust the thickness of the rings after the rings have been inserted within the cornea.

Figure 8A:
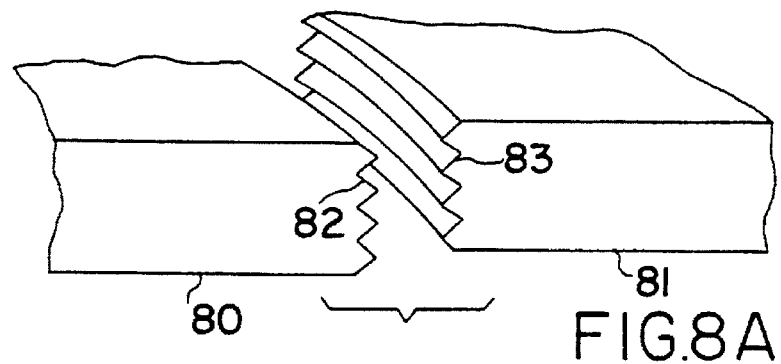
FIGS. 8A and 8B are perspective views showing a threaded height adjustment embodiment in two positions.
Figure 8B:
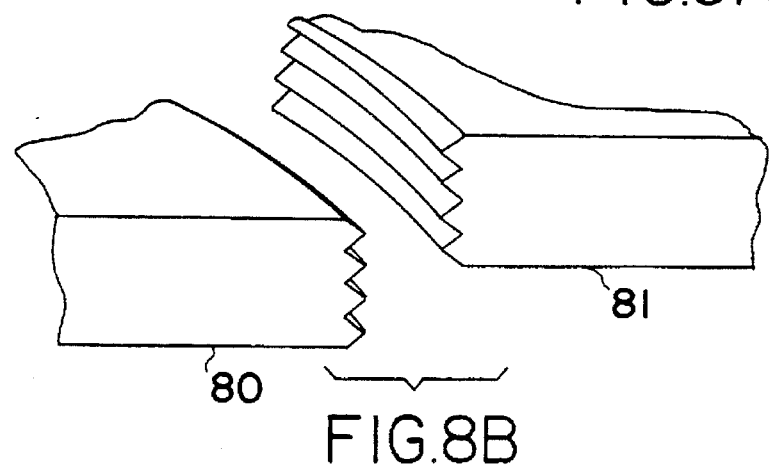

In FIG. 8A the rings 80 and 81 are shown in a cross sectional view. The inner ring 80 includes threadings 82 on its outer circumference while the ring 81 includes threadings 83 on its inner circumference. The threadings 82 and 83 mesh into each other and the rings 80 and 81 can be turned in directions opposite to each other. In the position shown in FIG. 8A the rings have been turned so that the ring 81 has been increased in height relative to the ring 82 thereby increase the thickness. This height adjustment can be carried out in In FIG. 9A the ring 90 is substantially deflated in that no fluid has been injected into the ring via the nozzle 91. In FIG. 9B the ring 90 has been substantially inflated by the injection of a fluid into the ring 90 via the nozzle 91. By injecting the fluid into the ring the thickness of the ring is increased. It is also possible to design the ring such that its outer end or inner diameters are also increased with the injection of fluid. There are two separate subembodiments of the inflatable ring which can provide particular advantages. In a first subembodiment, the ring is designed so that when it is inflated it will only increase in thickness and not increase radially. In the second subembodiment, the ring is designed such that when it is inflated, it will not increase in thickness but only increase radially. It is possible to design a cross breed subembodiment which allows a certain, predetermined degree of thickness increase and a certain, predetermined degree of radial increase, each within specific limitations designed to obtain a specific effect. The nozzle 91 is preferably a check valve, i.e. one-way valve which allows a fluid to be injected in but which will not allow a fluid to flow out. However, fluid could be extracted by inserting a hypodermic needle into the valve opening and vacuuming fluid from the interior of the ring 90. As shown within FIG. 9A the valve 91 is preferably positioned on a separate piece 92 which can then be completely encompassed by and sealed with respect to the outer walls of the ring 90. However, other embodiments are possible. The material injected into the ring 90 can be any suitable material including water and biocompatible liquids and gels. For example, see the gel injection system disclosed within U.S. Pat. No. 5,090,955 issued Feb. 25, 1992 which is incorporated herein by reference.

Figure 9A:
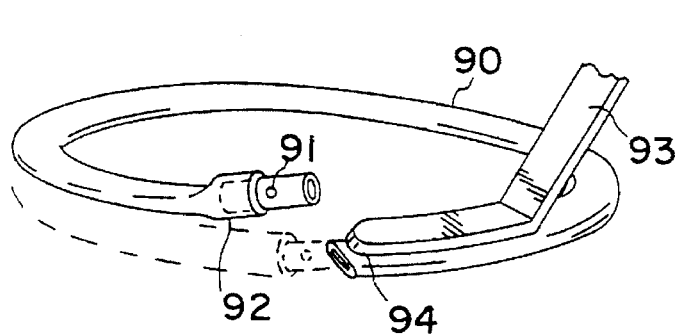
FIGS. 9A and 9B are perspective views of an inflatable embodiment in a deflated and inflated state.
Figure 9B:
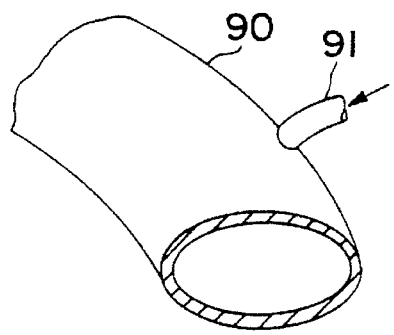

In FIG. 9A a method for including the inflatable ring 90 into the cornea of the eye is shown. In essence, the ring 90 is placed on a blade 93 which has a blade width approximately equal to or slightly larger than the internal diameter of the ring 90. The point 94 of the blade cuts annularly into the cornea followed by the ring 90. When a complete circular incision is made the entire ring 90 is inserted within that Thereafter, by holding the ring 90 in place the blade 93 can be withdrawn leaving the ring 90 in place. Thereafter, the interconnector including the nozzle 91 is inserted into one end of the ring and thereafter into the other ring in order to form a complete circle.

Figure 10:
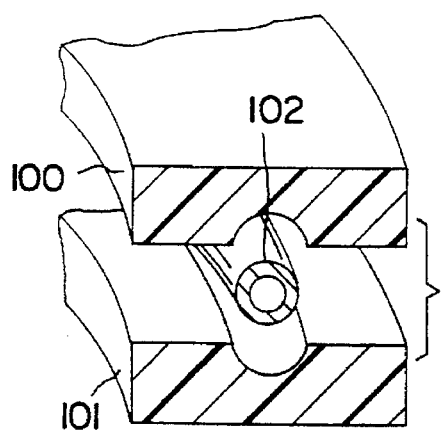
FIG. 10 is a cross sectional view of a tube centered embodiment.

A cross section of a tube centered embodiment is shown FIG. 10 wherein the upper ring 100 is separated from the lower ring 101 by a tube 102. In that the ring is placed within a relatively small incision within the ocular tissue, the components of the ring will be held together by the pressure provided by the ocular tissue. Accordingly, there is generally no need to provide any additional forces to bring the components together. However, the two rings can be held together by a supplemental means including by the inclusion of magnetic material within both of the rings. Alternatively the tube 102 may be comprised of a magnetic material and the rings 100 and 101 may include a material such as iron which is attracted by the magnetic material. In accordance with this embodiment the thickness of the overall ring structure is increased by increasing the size of the tubes 102 which are included between and separate the rings 100 and 101.

Figure 11A:
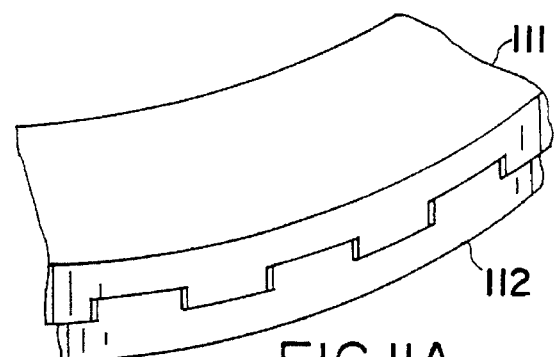
FIGS. 11A and 11B are perspective views of a notched embodiment in two positions.
Figure 11B:
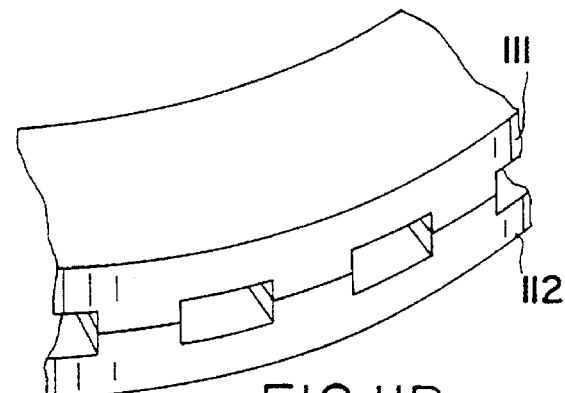

FIGS. 11A and 11B provide perspective views of the notched embodiment of the invention. In FIG. 11A the notches of the rings 111 and 112 are intermeshed to provide the thinnest possible ring structure. In FIG. 11B the notches are aligned so as to provide the maximum thickness. This embodiment may be easily constructed. However, it has disadvantages in that the adjustment is only in a single increment. This can be accounted for to a certain extent by including a plurality of notches of different heights and aligning the desired height notch in order to achieve the desired thickness and thereafter locking the rings into place by any appropriate means such as the use of sutures, adhesives, pins, etc.

Figure 12A:
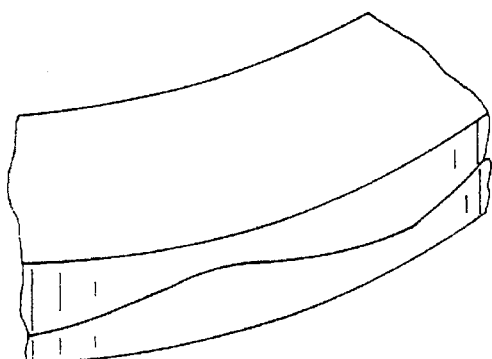
FIGS. 12A and 12B are perspective views of a smooth surface embodiment in two positions.
Figure 12B:
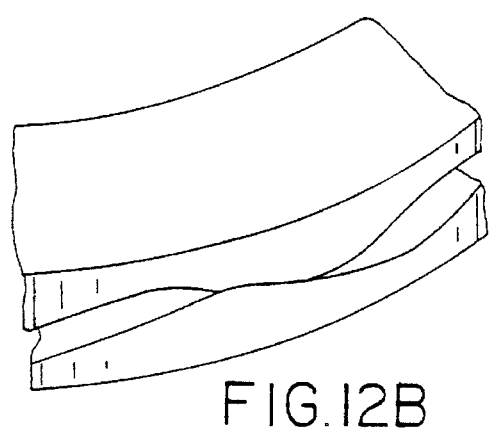

FIGS. 12A and 12B shows a smooth surface interlocking embodiment. In FIG. 12A the rings are intermeshed so as to provide the thinnest possible structure whereas FIG. 12B shows the thicker structure. Due to the smooth surfaces of the interlocking components it is possible to vary the height of the rings and when the desired height is achieved lock the rings into place by an appropriate means such as the use of an adhesive or sutures.

In all or any of the above embodiments variations are possible with respect to the cross sectional configuration of the rings, the type of material and other parameters. For example, all of the ring structures shown above must be open ended rings so that they can be inserted into the cornea via an entry incision and then fed around a circular incision made in the cornea. The ends may then be interconnected to each other. This can be done in a variety of ways. For example, the use of two rings makes it possible for each of the rings to act as a closure means for the other when the rings are rotated relative to each other so that their ends are not aligned. This can be done after inserting the rings in the eye. When two rings are not present (e.g. the inflatable embodiment) the ends of the ring can be interconnected as shown in FIG. 13.

FIG. 13 shows a tapered overlapping configuration. The tapered effects of the ends 130 and 131 is dramatically shown within FIGS. 13 and 13E. One end 130 gradually narrows at the same rate that the end 131 narrows. The ends 130 and 131 are held together by horizontal and vertical force vectors which oppose each other and are shown as hf, hf', vf and vf' as shown in FIG. 13A. The cross sectional structure of the ring can be circular as indicated by the different configurations in FIGS. 13B, 13C and 13D. However, as shown in these figures the manner in which the ends 130 and 131 fit together along their adjacent surfaces can vary from the planar interconnection of FIG. 13B to the curved plane of FIG. 13C and the peaked interconnection of FIG. 13D. A cross section is shown in FIG. 13E.

Figure 14A:
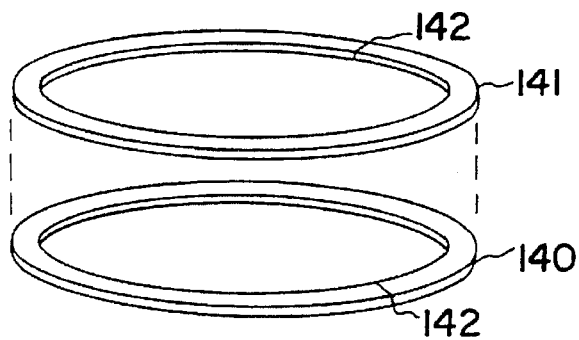
FIGS. 14A and 14B show a stacked shim embodiment of the invention with and without the shims in place.
Figure 14B:
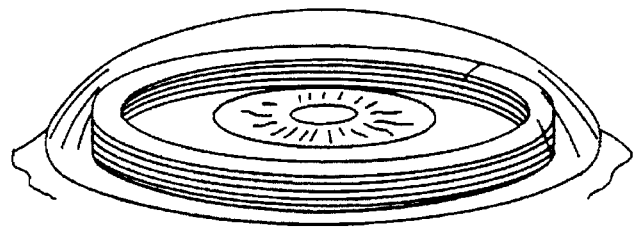

In FIG. 14A a stacked shim embodiment is shown. The embodiment includes at least a lower disk 140 and an upper disk 141. Each of the disks have openings in their center. The lower disk 140 may include a radially raised area (not shown) protruding upwardly. This raised area fits within an indentation (not shown) in the upper disk. Each of the disks are open ended, i.e. they are not continuous but have ends 142. The multiple disks 140 and 141 may be stacked on top of each other and inserted into the cornea, as shown within FIG. 14B. Thereby, the size of the ring structure inserted into the eye can be increased in thickness to any degree.

Figure 15A:
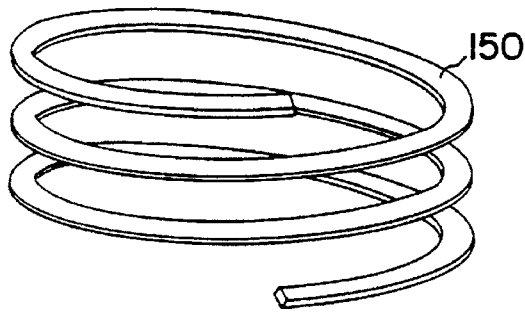
FIGS. 15A and 15B show a spiral spring embodiment of the invention in a collapsed position and as the spiral might be inserted.
Figure 15B:
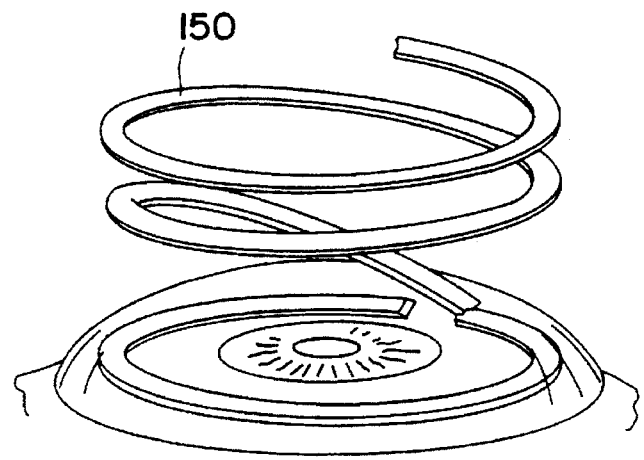

FIG. 15A shows a spiral shaped spring embodiment of the invention. This embodiment is comprised of a singular spiral or spring shaped piece of material 150. As shown within FIG. 15B the end of the spiral is inserted into the annular channel formed in the cornea and set into the channel. The device is continually fed into the channel in a manner such that each circular movement of the spring will cause another layer to be added making it possible to increase thickness to any desired amount. When the desired amount of thickness is obtained, the material is cut. The spiral ring 150 can be designed in a variety of different ways. For example, the ring can be designed so that each successive ring has the same diameter and fits tightly against the next ring. When this shaped device is used, the cornea is increased in thickness as additional layers are added but is not increased radially. In another embodiment, the spring-shaped piece of material 150 can be designed so that each successive ring is slightly larger in diameter. Thereby, increases in the diameter of the inserted ring can be obtained by including additional rings into the cornea.

Modifications of the above described modes for carrying out the invention may occur to persons of skill in the fields of medicine, ophthalmology, optometry and/or related fields upon reading the disclosure and are all intended to be within the scope of the following claims.

We claim:

1. An intrastromal corneal device, at least a portion of said device being adapted for placement in the cornea of an eye to change the refractive properties of the eye, said device comprising:

a flexible coil-shaped ring having a plurality of coils whereby the thickness of said portion placed into the eye depends on the number of coils inserted.

2. A corneal implant adapted for placement in the cornea of an eye to change the refractive properties of the eye, at least a portion of said implant comprising a spiral-shaped body.

3. The corneal implant of claim 2, wherein said spiral shaped body has overlapping arcuate portions.

4. The corneal implant of claim 3, wherein said spiral-shaped body includes multiple turns that form layers, each of said layers contributing to the overall thickness of said spiral-shaped body.

5. The intrastromal corneal implant of claim 4, wherein said layers have the same diameter.

6. The intrastromal corneal implant of claim 4, wherein at least one of said layers has a diameter larger than another of said layers.

* * * * *